United States Patent
Mintchev et al.

(10) Patent No.: US 9,107,820 B2
(45) Date of Patent: Aug. 18, 2015

(54) DEVICE FOR DELIVERY OF A SUBSTANCE

(71) Applicant: EatLittle Inc., Calgary (CA)

(72) Inventors: Martin Mintchev, Calgary (CA); Orly Yadid-Pechet, Calgary (CA); Michel Fattouche, Calgary (CA)

(73) Assignee: EatLittle Inc., Calgary, Alberta (CA)

( * ) Notice: Subject to any disclaimer, the term of this patent is extended or adjusted under 35 U.S.C. 154(b) by 0 days.

(21) Appl. No.: 14/312,189

(22) Filed: Jun. 23, 2014

(65) Prior Publication Data

US 2014/0330210 A1 Nov. 6, 2014

Related U.S. Application Data

(62) Division of application No. 12/517,752, filed as application No. PCT/CA2007/002336 on Dec. 18, 2007, now Pat. No. 8,795,721.

(60) Provisional application No. 60/875,311, filed on Dec. 18, 2006.

(51) Int. Cl.
| | |
|---|---|
| *A61K 9/54* | (2006.01) |
| *A61M 29/00* | (2006.01) |
| *A61K 9/22* | (2006.01) |
| *A61K 31/00* | (2006.01) |
| *A61K 9/00* | (2006.01) |
| *A61M 31/00* | (2006.01) |
| *A61L 31/14* | (2006.01) |
| *A61M 29/02* | (2006.01) |

(52) U.S. Cl.
CPC .............. *A61K 9/0065* (2013.01); *A61K 9/009* (2013.01); *A61L 31/146* (2013.01); *A61M 31/00* (2013.01); *A61M 31/002* (2013.01); *A61M 29/02* (2013.01)

(58) Field of Classification Search
CPC ... A61K 9/0065; A61K 9/009; A61K 9/2072; A61K 9/4808; A61K 9/0068; A61M 31/002; A61M 31/00; A61M 29/02; A61F 5/0036; A61F 5/0003; A61F 5/003
USPC ......... 424/473, 456, 484, 451, 457, 458, 482; 606/191, 192; 604/890.1, 891.1, 892.1
See application file for complete search history.

(56) References Cited

U.S. PATENT DOCUMENTS

| | | | | |
|---|---|---|---|---|
| 8,389,003 | B2 * | 3/2013 | Mintchev et al. | 424/451 |
| 8,691,269 | B2 * | 4/2014 | Mintchev et al. | 424/452 |
| 8,795,721 | B2 * | 8/2014 | Mintchev et al. | 424/458 |

* cited by examiner

*Primary Examiner* — Kevin C Sirmons
*Assistant Examiner* — William Carpenter
(74) *Attorney, Agent, or Firm* — Kyle R. Satterthwaite; Ryan W. Dupius; Ade & Company Inc.

(57) ABSTRACT

A device for delivering a substance in situ in a body comprising at least one permeable expandable container having a first dimension and a second dimension and having contained therein the substance to be delivered; and at least one expandable particle comprising a swellable material contained within the container and capable of expanding when contacted with a fluid; whereby when the device is positioned in situ, bodily fluid permeates the container causing the at least one expandable particle contained therein to swell and the container to expand from the first dimension to the second dimension so that the device remains in situ for a period of time sufficient to achieve the desired delivery of the substance is provided.

4 Claims, 20 Drawing Sheets

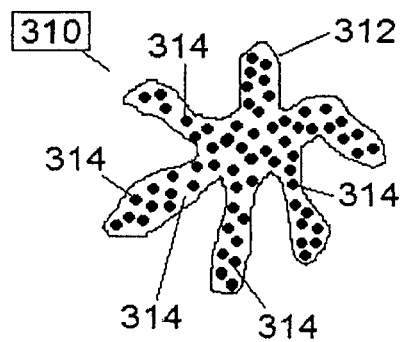
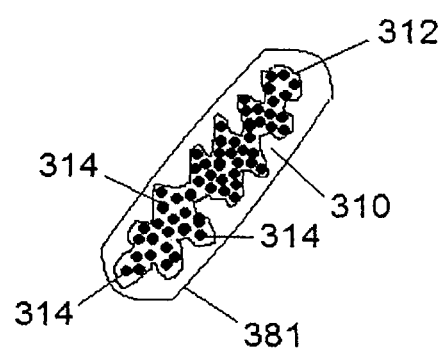
FIG.13A  FIG.13B
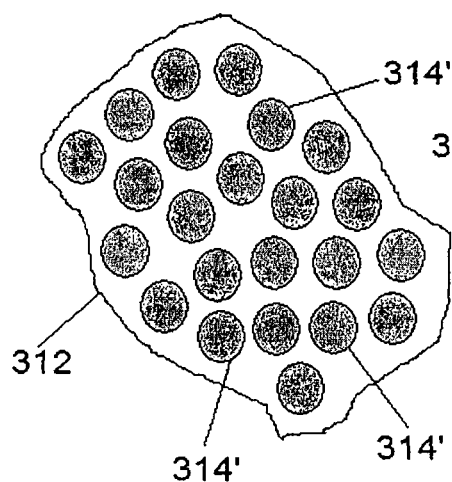
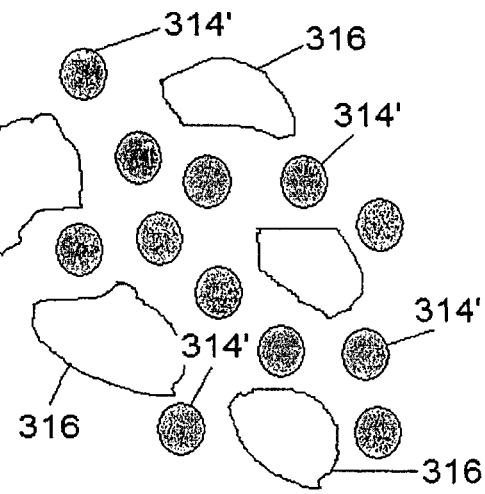
FIG.13C  FIG.13D

FIGS. 17 A & B
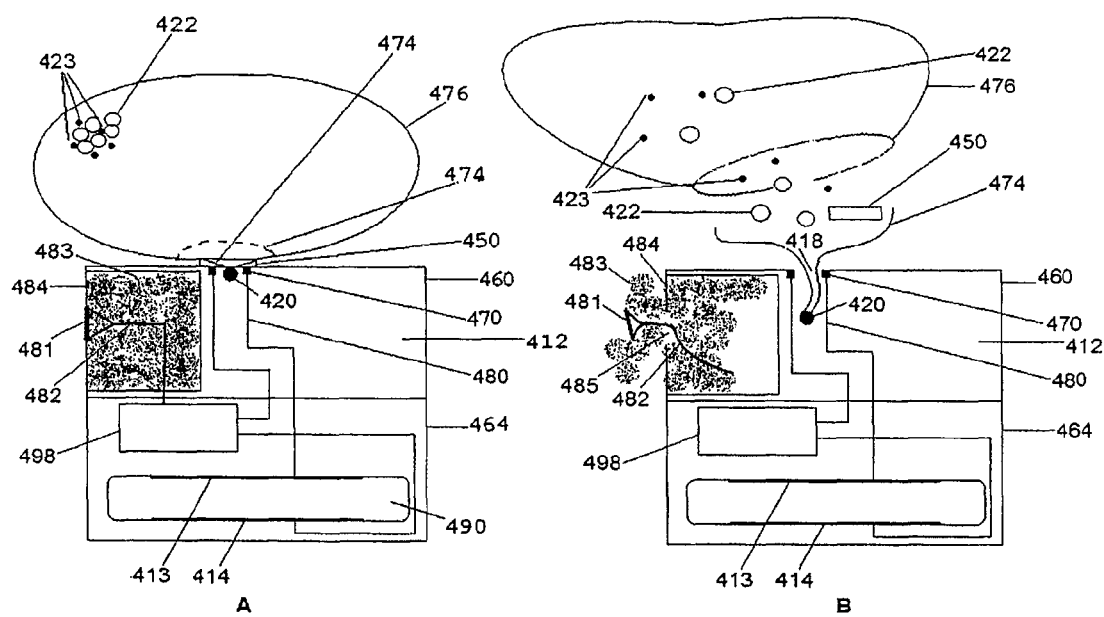

DEVICE FOR DELIVERY OF A SUBSTANCE

This application is a divisional of U.S. Non-provisional application Ser. No. 12/517,752, which is a 371 national stage of PCT/CA2007/002336 and claims benefit under 35 USC 119(e) of U.S. Provisional Application No. 60/875,311, filed Dec. 18, 2006, the disclosure of which is incorporated herein.

FIELD OF THE INVENTION

The present invention relates generally to a system of delivering substances such as drugs to the body. More specifically, the present invention relates to a substance delivery device for the controlled and timed release of a substance in situ.

BACKGROUND OF THE INVENTION

There exist a variety of devices for controlled release of specific substances such as drugs in the body (see, for example, US Patent Application Publications Nos. 20070241042; 20070239107; 20070237741; 20070225634; 20070218125; 20070218083; 20070213659; 20070212416; 20070207200; 20070196433; 20070193894; 20070184112; 20070174128; 20070173776; 20070154522; 20070149954; 20070128279; 20070110807; 20070106281; 20070106277- 20070106266; 20070088267; 20070050010; 20060285912; 20060210604; 20060198892; 20060182738; 20060178655; 20060124129; 20060116422; 20060115785; 20060034913; 20060030837; 20060029653; 20060020253; 20060003008; 20050273049; 20050249798; 20050222627; 20050205083; 20050158246; 20050149000; 20050148847; 20050147678; 20050107870; 20050070996; 20050058701; 20040253304; 20040219186; 20040204750; 20040180088; 20040161382; 20040138733; 20040086562; 20040077513; 20040032187; 20040024382; 20040022853; 20040005359; 20030216683; 20030172924; 20030133979; 20030120339; 20030036746; 20020183682; 20020168410; 20020123678; 20010020147; and 20010002262).

There may be times when it is desirable to continuously administer a substance such as drug to a patient over a long period of time. Further, there may be times when it is desirable to deliver a substance at specified time intervals over a period of time. Most prior art devices are not capable of remaining in the body (e.g., in a cavity or orifice) long enough to provide continuous release over extended periods of time. Further, most devices lack a precise feedback control mechanism to achieve completely controlled release of a substance from the device.

Consequently, the need has arisen for a substance delivery device that allows controlled delivery of specific substances in a given orifice or cavity in the body in situ to address some of the problems encountered in the prior art.

SUMMARY OF THE INVENTION

This application is directed to a device for delivering a specific substance to the body which can be positioned in a given orifice or cavity of the body. Without being limiting, the delivered substance can be a medicinal, therapeutic, pharmaceutical, or nutritional substance, or combinations thereof. Once the device is positioned, the specific substance can be released into the body by a number of triggering stimuli, for example, electrical, chemical, electrochemical, magnetic, electromagnetic, mechanical, or combinations thereof. The release of the specific substance can be implemented by a variety of mechanisms, for example, a delay mechanism after the unit is positioned in a given cavity or orifice in the body, or a built-in closed-loop control mechanism to release the substances on an "as needed" basis, for example, as a result from real-time measurement of a given physiological parameter, such as acidity, temperature, enzymes, etc. and subsequent decision-making to release the necessary quantity of a given medicinal, therapeutic or pharmaceutical substance. The measurement of a given physiological parameter can be performed by a specific sensor that may be integrated with the device, which is discussed in more detail below.

According to a broad aspect of the invention, there is provided a device for delivering a substance in situ in a body, comprising:
- at least one permeable expandable container having a first dimension and a second dimension and having contained therein the substance to be delivered; and
- at least one expandable particle comprising a swellable material contained within the container capable of expanding when contacted with a fluid;

whereby when the device is positioned in situ, bodily fluid permeates the container causing the at least one expandable particle contained therein to swell and the container to expand from the first dimension to the second dimension so that the device remains in situ for a period of time sufficient to achieve the desired delivery of the substance.

In one embodiment, the substance is releasably associated with the expandable particle. In another embodiment, the substance is releasably associated with at least one substance carrying particle, which is also contained within the container and may or may not be associated with the expandable particle. In another embodiment, the substance may be releasably associated with the container itself. In another embodiment, the substance may be contained in the container as formulated granules, which granules may be fast release, controlled release or extended release, as is known in the art.

In another embodiment, two or more containers are releasably coupled to each other by a coupling member such as a piece of absorbable biodegradable surgical suture, a piece of biodegradable medical gauze, an absorbable net-like nanostructure or biocompatible glue known in the art. It is understood, however, that the two or more containers can be releasably coupled to one another by other coupling members known in the art. For example, each container may contain a small magnet and the magnets can attract one another to couple the containers.

In another embodiment, the at least one container is releasably coupled to a carrier by a piece of absorbable biodegradable surgical suture, a piece of biodegradable medical gauze, an absorbable net-like nanostructure, biocompatible glue and the like. In one embodiment, the device further comprises a decoupler for decoupling the at least one container from the carrier once the desired period of time has expired, thereby releasing the at least one container and carrier into the body for removal. In one embodiment, the container is made from a dissolvable material to allow for the eventual release of the at least one expandable particle from the container.

According to another broad aspect of the invention, there is provided a device for delivering a substance in situ in a body, comprising:
- at least one permeable expandable container having a first dimension and a second dimension containing at least one expandable particle comprising a swellable material capable of expanding when contacted with a fluid;
- at least one substance-holding container containing the substance to be delivered; and
- at least one coupling member for coupling the at least one permeable expandable container and the at least one substance holding container to form a single unit;

whereby when the device is positioned in situ, bodily fluid permeates the at least one permeable expandable container causing the at least one expandable particle contained therein to swell and the at least one permeable expandable container to expand from the first dimension to the second dimension so that the device remains in situ for a period of time sufficient to achieve the desired delivery of the substance.

In one embodiment, the substance contained in the substance holding container is releasably associated with at least one substance carrying particle. In another embodiment, the substance may be contained in the substance-holding container as formulated granules, which granules may be fast release, controlled release or extended release, as known in the art.

In one embodiment, the substance-holding container is made from a permeable material so that the substance can begin release as soon as the device is positioned in situ in the body. In another embodiment, the substance holding container is made from a non-permeable material and the substance will only be released when the integrity of the substance-holding container becomes compromised.

For example, without being limiting, in some instances the coupling member may serve a dual function; it may serve both to close the substance holding container to contain the substance and to couple the substance holding container to another substance-holding container, to the at least one permeable expandable container or to a separate carrier. When the coupling member disintegrates, as would be the case if the coupling member were made from a piece of absorbable biodegradable surgical suture, a piece of biodegradable medical gauze, an absorbable net-like nanostructure, biocompatible glue and the like, the integrity of the substance-holding container becomes compromised (i.e., it opens) and the substance is released.

In one embodiment, at least one coupling member comprises a carrier having a cavity. In this embodiment, the carrier can further comprise at least one decoupler located in the cavity for decoupling the at least one permeable expandable container, the at least one substance-holding container, or both. For example, without being limiting, the decoupler can be programmed to first release the at least one substance-holding container so that the substance contained therein can be released. It can then decouple the at least one permeable expandable container so that all of the components of the device can either be removed from the body or absorbed by the body.

According to another aspect of the invention, there is provided a device for delivering a substance in situ in a body, comprising:

a carrier having an interior cavity for holding at least a portion of the substance to be delivered;

at least one permeable expandable container having a first dimension and a second dimension releasably attached to the carrier by a coupling member; and at least one expandable particle comprising a swellable material contained within the container capable of expanding when contacted with a fluid;

whereby when the device is positioned in situ, bodily fluid permeates the at least one permeable expandable container causing the at least one expandable particle contained therein to swell and the at least one permeable expandable container to expand from the first dimension to the second dimension so that the device remains in situ for a period of time sufficient to achieve the desired delivery of the substance.

The substance contained in the carrier may be releasably associated with at least one substance carrying particle or it may be contained in the carrier as formulated granules, which granules may be fast release, controlled release or extended release, as known in the art. The substance carrying particle can be made of a dissolvable material.

In this embodiment, the substance is released from the carrier when one or more of the at least one permeable expandable container is decoupled from the carrier.

According to another broad aspect of the present invention, there is provided an orally-administrable pharmaceutical dosage form including at least one substance delivery device of the present invention and, if desired, a pharmaceutically acceptable excipient such as binders, fillers and disintegrants, for example, starch. The pharmaceutical dosage form may take various forms, which include, but are not limited to, liquids, soft substances, powder-like substances, and hard pharmaceutical substances such as soft capsules, hard capsules and tablets. In one embodiment, the pharmaceutical dosage form is a capsule. In another embodiment, the capsule can be coated with a pH-sensitive coating. The pH-sensitive coating may prevent dissolution until the stomach reached, to prevent contact between the swellable clusters and aqueous solutions.

According to another broad aspect of this invention, there is provided a method for delivering a substance in a given cavity or orifice of the body, the method comprising the steps of: (a) administering at least one substance delivery device as described above into the cavity or orifice; (b) contacting the substance delivery device with bodily fluids to allow for the expandable particles to swell and prevent the substance delivery device from exiting the orifice or the cavity; (c) allowing specific substance to be released from the substance releasing device; and (d) after a desired period of time, allowing the substance delivery device to disassemble so that it can harmlessly exit from the body or be rapidly absorbed. In one embodiment, delivery of specific substance is maintained for a pre-determined therapy duration by systematically and periodically introducing into the cavity or orifice additional substrate delivery devices.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The present invention, both as to its organization and manner of operation, may best be understood by reference to the following description, and the accompanying drawings of various embodiments wherein like reference numerals are used throughout the several views, and in which:

FIG. 13A is a schematic view of an embodiment of a substance delivery device comprising a permeable expandable container containing dry expandable particles impregnated with a specific substance.

FIG. 13B is a schematic view of the substance delivery device of FIG. 13A, which can be inserted into an AAA gelatin capsule for oral administration.

FIG. 13C is a schematic view of the substance delivery device of FIG. 13A in its expanded state.

FIG. 13D is a schematic view showing the disintegration of the permeable expandable container of the expanded device shown in FIG. 13C after a predetermined period of time and the dispersion of the individual expandable particles impregnated with the substance.

FIG. 17A is a schematic view of an embodiment of a substance delivery device where the substance to be delivered is contained in a carrier.

FIG. 17B depicts the release of the substance from the substance delivery device shown in FIG. 17A.

DESCRIPTION OF THE PREFERRED EMBODIMENTS

Figure 1A:
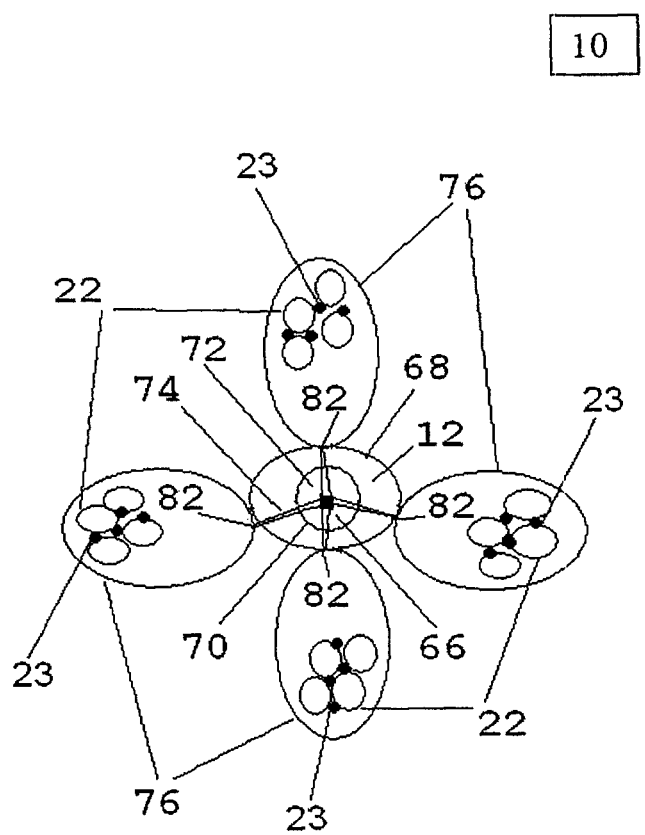
FIG. 1A is a schematic view of one embodiment of a substance delivery device according to the invention in the expanded state, where the expandable particles and the substance carrying particle are both present in the same permeable expandable container.

It is understood that the device of the present application can be positioned in an orifice or cavity of a body of an animal, including a human, in order to deliver a substance in situ. The orifices or cavities in the body where the device can be positioned include, but are not limited to: mouth, ear canals, skull, gastrointestinal tract, wounds, teeth cavities, vagina, anus, stoma, eye cavities, kidneys, testicles, prostate, lungs, transplanted organs, etc. The device, once positioned in situ in the body, expands so that it remains in situ until such time as the substance has been released into the body. The bodily fluids facilitating the expansion of the device include, but are not limited to, blood, puss, saliva, ocular fluids, gastrointestinal liquids, urine, vaginal fluids, semen, etc.

The expandable particles can be made of Bentonite, a biocompatible polymer, starch, or a combination thereof. For example, which is not meant to be limiting, the expandable particles can be made of super-absorbent and filler material such as microcrystalline hydrogels and polyolefins. The expandable particles can also be biodegradable to facilitate their expulsion out of, or absorption by, the body. In one embodiment, the expandable particles have a controlled rate of dissolving and when present in a carrier can exit the carrier only after getting reduced beyond certain dimension.

The substance carrying particles can comprise a large variety of different materials, and can include, but are not limited to, polycaprolactone spheres, impregnated with a specific desirable substance. Other suitable substance carrying particles comprise pharmaceutically acceptable polymers, that may be selected from the group consisting of polylactic acid, polyglycolic acid, polylactic-co-glycolic acid, polylactic acid-co-caprolactone, polyethylene glycol, polyethylene oxide, polyvinyl pyrrolidone, polyorthoesters, polysaccharides, polysaccharide derivatives, polyhyaluronic acid, polyalginic acid, chitin, chitosan, cellulose, hydroxyehtylcellulose, hydroxypropylcellulose, carboxymethylcellulose, polypeptides, polylysine, polyglutamic acid, albumin, polyanhydrides, polyhydroxy alkonoates, polyhydroxy valerate, polyhydroxy butyrate, proteins, and polyphosphate esters.

The term "substance" is used herein to define any medicinal, therapeutic, pharmaceutical or nutritional substance, or combinations there, that is delivered to a bodily conduit of a living being to produce a desired, usually beneficial, effect. The therapeutically active substances used in the present invention include classical low molecular weight therapeutic agents commonly referred to as drugs including all classes of action as exemplified by, but not limited to: antineoplastic, immuno-suppressants, antiproliferatives, antithrombins, antiplatelet, antilipid, anti-inflammatory, angiogenic, anti-angiogenic, vitamins, ACE inhibitors, vasoactive substances, antimitotics, metello-proteinase inhibitors, NO donors, estradiols, anti-sclerosing agents, alone or in combination. Therapeutic agent also includes higher molecular weight substances with drug like effects on target tissue sometimes called biologic agents including but not limited to: peptides, lipids, protein drugs, enzymes, oligonucleotides, ribozymes, genetic material, prions, virus, bacteria, and eucaryotic cells such as endothelial cells, monocyte/macrophages or vascular smooth muscle cells to name but a few examples. The therapeutic agent may also be a pro-drug, which metabolizes into the desired drug when administered to a host. In addition, the therapeutic agents may be pre-formulated as a microcapsules, microspheres, microbubbles, liposomes, niosomes, or the like. The therapeutically active substance may also be radioactive isotopes or agents activated by some other form of energy such as light or ultrasonic energy, or by other circulating molecules that can be systemically administered.

The present invention is particularly well suited for the delivery of, which list is not meant to be limiting, antifungal agents such as fluconazole, which has been shown to be capable of destroying a variety of fungal microorganisms, such as *Candida albicans*; pH reducing substances such as omeprazole; and weight-reducing substances such as orlistat, etc. Another example of a desirable substance that works well in a slow release device, such as the one described herein, is anti-oxidant materials that promote longevity, as documented in a number of research papers. Another example of a substance that works better if one uses timed and prolonged controlled release is the anti-obesity medication orlistat, which can be released in a delayed and timed fashion from the device when present in the stomach, rather than passing quickly through the gastrointestinal tract and being only partially absorbed.

Typical formulations for therapeutic substances incorporated in these substance delivery devices are well known to those skilled in the art and include but are not limited to solid particle dispersions, encapsulated agent dispersions, and emulsions, suspensions, liposomes or microparticles, wherein said liposome or microparticle comprise a homogeneous or heterogeneous mixture of the therapeutic agent.

The amount of the drug that is present in the device, and that is required to achieve a therapeutic effect, depends on many factors, such as the minimum necessary dosage of the particular drug, the condition to be treated, the chosen location of the inserted device, the actual compound administered, the age, weight, and response of the individual patient, the severity of the patient's symptoms, and the like.

The appropriate dosage level of the therapeutic agent, for more traditional routes of administration, are known to one skilled in the art. These conventional dosage levels correspond to the upper range of dosage levels for compositions, including a physiologically active substance and traditional penetration enhancer. However, because the delivery of the active substance occurs at the site where the drug is required, dosage levels significantly lower than a conventional dosage level may be used with success. Ultimately, the percentage of therapeutic agent in the composition is determined by the required effective dosage, the therapeutic activity of the particular formulation, and the desired release profile. In general, the active substance will be present in the substance carrying particles in an amount from about 0.0001% to about 99%, more preferably about 0.01% to about 80% by weight of the total composition depending upon the particular substance employed. However, generally the amount will range from about 0.01% to about 75% by weight of the total composition, with levels of from about 25% to about 75% being preferred.

When positioning in the stomach is desirable, the device can be swallowed in a capsule, which capsule dissolves in the stomach. Then the device expands in the gastric cavity due to the absorption of gastric liquids, and the drug-delivery device is formed as a gastric bezoar, which cannot exit the stomach until it disintegrates. Thus, during the prolonged stay in the stomach of this gastric bezoar device, various specific substances can be delivered to the body in a timed and controlled fashion.

The substance carrying particles may be made of a dissolvable material and can be (a) packed together with the expandable particles in biocompatible, permeable and absorbable sacs that serve as permeable expandable containers; (b) impregnated to the expandable particles that are packed in biocompatible, permeable and absorbable sacs that serve as permeable expandable containers; (c) separately contained in a carrier; or (d) packed in small non-permeable but absorbable sacs that serve as substance holding containers, made, for example, from polyvinyl alcohol, knitted oxidized regenerated cellulose yarn, or from knitted polyglycolic acid yarn, which can open so that the substance carrying particles are released only providing certain conditions are met. For example, without being limiting, if the pH in the stomach falls below 1.5, one such substance holding container is opened in a controlled fashion and substance carrying particles can release a substance such as a strong antacid medication into the stomach. This would lead to a temporary increase of gastric pH. Should the pH fall below 1.5 again, another substance holding container containing antacid carrying particles is opened in a controlled fashion. This process of feedback-controlled release can continue until all small non-permeable sacs containing the specific medicinal substance are opened.

The coupling members can be made from a variety of materials, for example, without being limiting, absorbable biodegradable surgical sutures, biodegradable medical gauze, an absorbable net-like nanostructure, biocompatible glue and the like. In one embodiment, the coupling members are magnets contained within each container for coupling two containers together.

The device may further comprise a carrier. The carrier may adopt a wide variety of different shapes, which can include, but are not limited to, sphere, pyramid, cylinder and cube shapes or combinations thereof. In one embodiment, the carrier comprises an inner cavity for housing a physiological sensor, a feedback-processing component, a decoupler, etc.

The physiological sensor can measure any number of physiological conditions, for example, without being limiting, chemical, physical, electronic, electrochemical, and electrophysiological conditions. The physiological sensor can be used to control the release of specific substances by a closed-loop feedback control mechanism. For example, in one embodiment pertaining to the gastric cavity, the physiological sensor can comprise a miniature antimony electrode for measuring pH using a commercially available measurement technology (Bodger and Trudgill, Guidelines for Oesophageal Manometry and pH Monotoring, BSG Guidelines in Gastroenterology, November, 2006, incorporated herein by reference). The pH measurement provided by the antimony electrode is then processed by a feedback-processing component operably associated with the sensor, and a decision is made whether to release a substance holding container containing antacid carrying particles or not.

The decoupler may also be operably associated with the carrier and can be quite diverse. The decoupler may operate to decouple the permeable expandable container, the substance holding container, or both. The decoupler specific for the release of both the permeable expandable container and the substance holding container is generally similar in nature to the decoupler for the substance holding containers alone. When such a decoupler is activated, the entire device disintegrates, and the pieces that it is comprised of either exit the body cavity or orifice in which they were positioned naturally, or are absorbed by the body, without creating any obstruction or infection.

The decoupler for the non-permeable substance holding containers containing medicinal substances, which may be operably associated with the carrier, can be quite diverse, and can comprise absorbable surgical suture, absorbable nanostructure, electronic microheater, micro-electromechanical enclosure, or combinations thereof.

DESCRIPTION OF THE PREFERRED EMBODIMENTS

The following embodiments of the substance delivery device are designed to expand in any orifice or cavity in the body of an animal, including a mammal, to fill a space and to deliver specific substances. When the device expands in the given orifice or cavity, the expanded size of the device is such that exiting of the expanded device from the said orifice or cavity is prevented, which creates a substance-delivery platform in the cavity or orifice for delivering a substance for a specified period of time. After a desired amount of time has passed, the device disintegrates, releasing the expanded expandable particles and other dissolvable particles, if present, from the containers. This disintegration can allow the released parts of the device to now exit the given cavity or orifice in the body and eventually leave the body naturally, or be easily absorbed by the body.

When both types of particles (expandable and dissolvable) are released from the containers, they, as well as the containers themselves, can individually exit the body or be absorbed by it.

The decouplers for the release of substance-holding containers carrying the specific medicinal substance can be quite diverse, but their main feature is easy, energy-efficient and timed control. The decouplers for the release of permeable expandable containers containing expandable particles can also vary widely. For example, when the coupling member is absorbable surgical suture or absorbable gauze, and the timing for decoupling can be estimated by knowing the reduction in the tensile strength of the absorbable surgical suture or absorbable gauze. The feedback and decision-making mechanism used to selectively decouple substance-holding containers carrying the specific substances can also vary widely, and can be based on the readings of physical, chemical, electrochemical, electrophysiological, or electronic microsensors.

The substance delivery devices are useful for the controlled delivery of specific substances in situ and can also be useful for the facilitation of weight loss and the treatment of obesity when delivered into the stomach. The substance delivery device can be a non-invasive treatment for obesity that can be timed, which can result in less discomfort to the subject ingesting the unit and the ability to design a specific diet plan utilizing this technology.

Figure 1B:
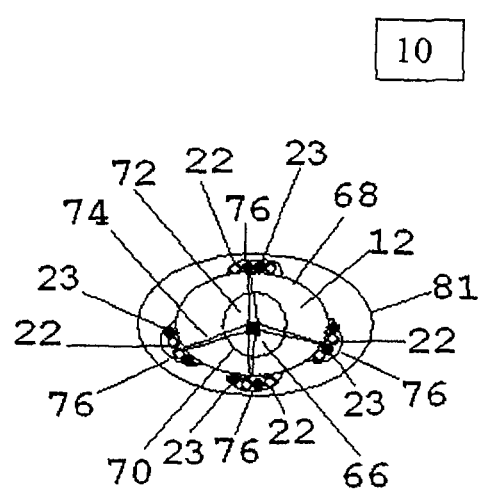
FIG. 1B is a schematic view of the substance delivery device of FIG. 1A in the non-expanded state and encapsulated in a capsule.
Figure 2:
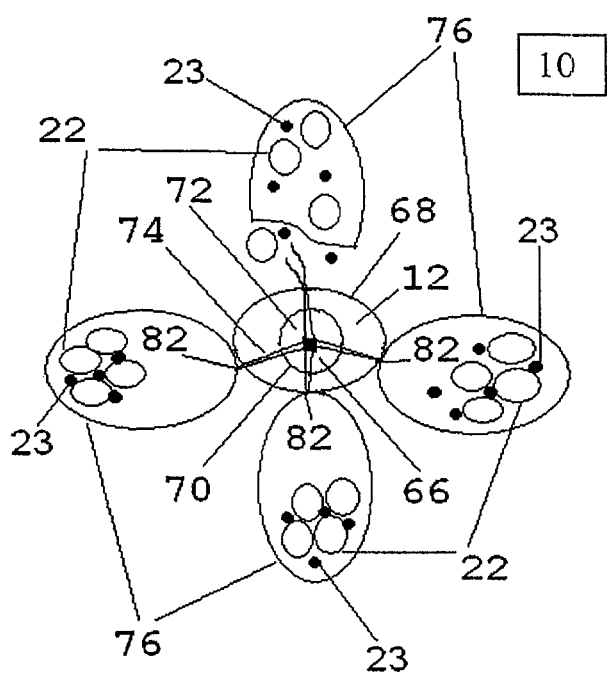
FIG. 2 is a schematic view of the substance delivery device of FIG. 1A where the coupling member comprises absorbable surgical suture that is interrupted at a single point due to its decaying tensile strength.
Figure 3:
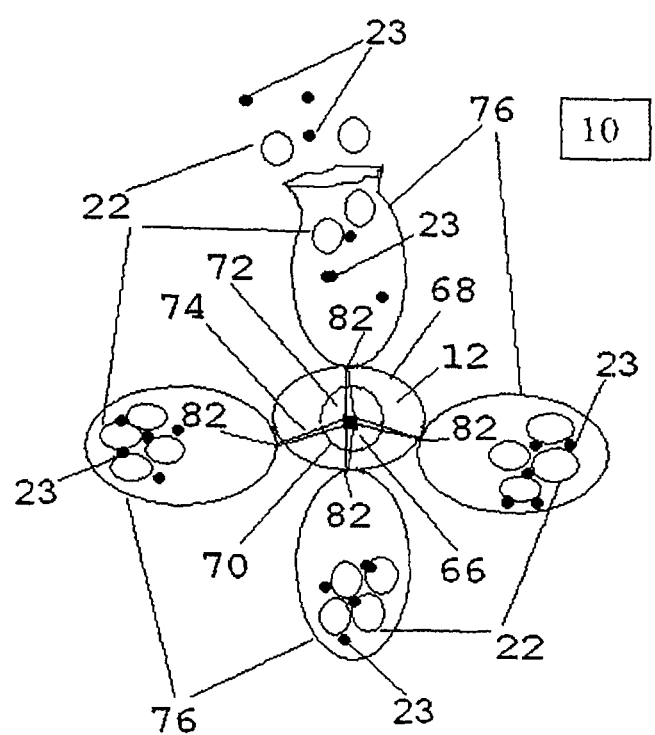
FIG. 3 is a schematic view of the orally administrable implement of FIG. 1A where the permeable expandable container is made of an absorbable medical gauze capable of disintegrating and releasing the particles therein.

With reference to the embodiment as shown in FIGS. 1-3, the substance delivery device, referred to generally as element 10, includes a carrier 12 having an outer surface 68 and an inner surface 70, with the inner surface forming an internal cavity 72. In this embodiment, expandable particles 22 are carried in a plurality of permeable, biocompatible, biodegradable, expandable sacs or containers 76 that are releasably coupled to the carrier 12 by at least one surgical suture (coupling member) 74 having two ends, one for tying the sacs closed and the other for attaching to the carrier. Once the device 10 is positioned in the body, bodily fluids allow the expandable particles 22 to swell or expand and the sacs 76 to expand from a first dimension (as shown in FIG. 1B) to a second dimension (as shown in FIG. 1A). In its expanded state, the device 10 will remain in situ in the body until it is disassembled, as discussed below. This allows the substance to be released over a period of time until disassembly of the device.

Also contained in sacs 76 are dissolvable, substance carrying particles 23. The substance carrying particles 23 can either be free floating in the sacs 76 or releasably associated with expandable particles 22. The decoupling mechanism separates the absorbable surgical sutures 74 from the carrier 12 such that sacs 76 are now both released from the carrier 12 and opened to allow the release of both the expandable particles 22 and substance carrying particles 23. Desirably, sutures 74 are arranged so as to maximize coverage of carrier 12 with sacs 76.

As illustrated in FIGS. 1-3, sutures 74 can be threaded through internal cavity 72 of the carrier to form a closed loop so that at least one segment of sutures 74 is located within the internal cavity. Double-threaded sutures 74 can enter carrier 12 at a single location 82 for each sac, and can be knotted within the mechanical enclosure 66. Of course, if desired, more than one entry location per sac can also be used. The sutures connecting each individual sac may or may not be of same long-term tensile decay characteristics, so that full or partial disintegration of the device is achieved. In addition to the mechanical enclosure 66 holding the suture knots, the internal cavity 72 may or may not host a microelectronic feedback-providing mechanism registering the exact moment of disintegration, as will be discussed below.

In the embodiment illustrated in FIGS. 1-3, expandable particles 22 can include any material that can expand or swell when in contact with bodily fluids, and can include, but are not limited to, natural clays (for example, which is not meant to be limiting, Bentonite), microcrystalline hydrogels, polyolefins, polyvinyl alcohol, poly(ethyloxazoline), polyvinylacetate-polyvinylalcohol copolymers, poly(2-hydroxyethylacrylate), poly(2-hydroxyethylmethacrylate), polyacrylic acid, and copolymers thereof, polysaccharides, water soluble proteins, polynucleic acids, or a combination thereof. Expandable particles 22 can be made, if desired, of polyacrylic acid and a crosslinker by solution or suspension polymerization, using the type and quantity of crosslinker to control the swelling capacity and the gel modulus. The synthesis and use of such expandable particles have been previously described in the following references, incorporated herein by reference: (1) Buchholz and Peppas, Superabsorbent Polymers, ACS Symposium Series, 1994; (2) Buchholz and Graham, Modern Superabsorbent Polymer Technology, John Wiley & Sons, 1998; and (3) Biocompatible/Biodegradable Materials (Tutorial). Sigma-Aldrich, 2005, available online at:
http://www.sigmaaldrich.com/Area_of_Interest/Chemistry/Materials_Science/BiocompatibleBiodegradable/Tutorial.html.

Dissolvable, substance carrying particles 23 can include any material that has known long-term dissolving properties, such as polycaprolactone, which can be impregnated with any desired substance that is to be delivered. For example, but not limited to, the substance carrying particles can be impregnated with the specific substances such as antacid medication omeprazole, antifungal drug fluconazole, antiobesity drug orlistat, lipid absorption substance chitosan, anti-inflamatory analgesic drugs such as diclofenac, various antibiotics, probiotics, etc. The impregnation of the swellable particles with specific substance to be released can take place by various means, for example, using the process described by Rodriguez et al, *J Control Release*. 2003 Jan 17; 86(2-3):253-65.

The permeable expandable sacs or containers 76 can be made of an absorbable expandable permeable liner (absorbable medical gauze). The permeable liner should be able to allow bodily fluids to enter sacs 76 and contact the expandable particles 22 to allow for their expansion. In one embodiment, the permeable expandable sacs 76 can be made from natural cellulose fiber or specialty fiber through spun laced process, spun-bonded polypropylene or absorbable haemostatic oxidized regenerated cellulose (commercially available under the name Curacel), and are initially folded (first dimension), containing the non-expanded expandable particles 22 and the substance carrying particles 23. It may be desirable that the material itself used to construct sacs 76 be expandable, so as to concurrently expand with the expandable particles 22.

As a safety feature, sacs 76 may be made of biodegradable material, so as to allow for biodegradation after several days or weeks. Moreover, suture 74 is also made of an absorbable biocompatible material, which can include, but are not limited to polycaprolactone, polyglycolide, polylactide, or combinations thereof (commercially available under the names Selecture PLL and Selecture VEH by Schering-Plough Animal Health Corporation), or the like, each of which is absorbable and has specific tensile strength decaying characteristics that are not necessarily the same. Thus, if sutures of different tensile strength decaying characteristics are used, gradual partial disintegration of the device can result. It is imperative for sutures 74 to be capable of withstanding the maximum forces present in the given orifice or cavity of the body to prevent release of sacs 76 before the said suture biodegrades sufficiently so that the decoupling takes place. In one embodiment, if a single sac is used to contain the expandable particles 22 and the substance carrying particles 23, the decoupling mechanism could be the biodegradation of the sac itself.

The decoupling mechanism for decoupling the sacs 76 carrying the expandable particles 22 and the substance carrying particles 23 from carrier 12 include but are not limited to the natural biodegradation of the holding suture, or of the said sacs holding the clusters of molecules together, or of a combination thereof. Once suture/s 74 is/are disrupted, sacs 76 become separated from the carrier 12, they open, and the expandable particles 22 and the substance carrying particles 23 contained therein are dispersed in situ. Since each of these particles are smaller than a specific, physiologically determined size, they can individually exit the given orifice or cavity in the body in a natural way, or be absorbed by the body. The sutures 74 can be disrupted either sequentially or simultaneously. The sutures 74 can be disrupted inside the carrier using, for example, which is not meant to be limiting, a time-controlled microheater. The at least one suture 74 can be threaded through a thin-wire miniature heater, which can be isolated with ceramic cover so that the temperature inside the enclosed heater can quickly rise above 60 degrees Celsius, when the device is supplied with electrical power. If polycaprolactone absorbable surgical sutures are utilized with a melting temperature of 55 degrees Celsius, the microheater would provide the necessary temperature to melt the surgical suture, thus causing the structure that is held by it to fall apart. Alternatively, the device structure can be supported also by at least one surgical suture, which, however, is attached to a miniature piece of thin electric wire. When connected to a battery, this electric wore plays the role of a fuse, and gets disrupted, thus causing the device structure to fall apart.

As illustrated in FIG. 1B, substance delivery device 10 comprising permeable sacs 76 attached to the carrier 12, can be contained within a shell 81 in its dry, non-expanded state, with sacs 76 holding the dry expandable particles 22 and the substance carrying particles 23 together in a folded conformation. Shell 81 can be made of a variety of different materials, which can include, but are not limited to, pH-sensitive materials that will only dissolve under certain conditions, for example, the pH of the stomach. The material used to make the shell can be the same material, for example, gelatine or cellulose, used to make stomach-targeting pharmaceutical capsules known in the art. Various sizes of shells can be used.

FIG. 2 illustrates the opening of the permeable sacs 76 by disrupting the suture 74, thereby allowing the sac 76, which is held to the carrier at location 82, to open and release both the expandable particles 22 and the substance carrying particles 23. In this embodiment, the role of the carrier is to hold together all sutures 74.

In the embodiment illustrated in FIG. 3, the permeable sacs 76 disintegrate while the sacs 76 are still attached to carrier 12 by sutures 74, thereby releasing both the expandable particles 22 and the substance carrying particles 23. In this embodiment, the role of the carrier 12 is to serve as an attachment point of the permeable sacs 76.

Figure 4:
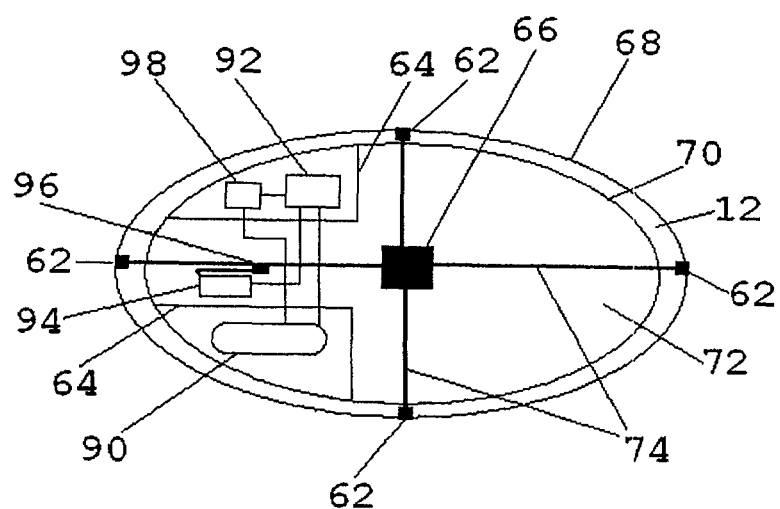
FIG. 4 is a schematic view of a carrier comprising one microelectronic system used to provide feedback for decoupling a container from the carrier.

FIG. 4 schematically illustrates one possible mechanism for providing microelectronic feedback information from a substance delivery device of the present invention to the external world about the exact moment of disintegration of the device. Battery 90 supplies a microcontroller 92 through a microswitch 94 which has a lever 96 that is connected to the suture 74 in such manner that when the device is intact, the microelectronic components are not turned on. Once the tensile strength of suture 74 diminishes and it becomes loose, the microswitch 94 flips back, turning on the microcontroller 92, which controls a radio-frequency (RF) transmitter 98, sending a message to the external world that disintegration of the device has occurred. Suture 74 is threaded through openings in the carrier 12, which are sealed by biocompatible silicon sealant 62.

Figure 5:
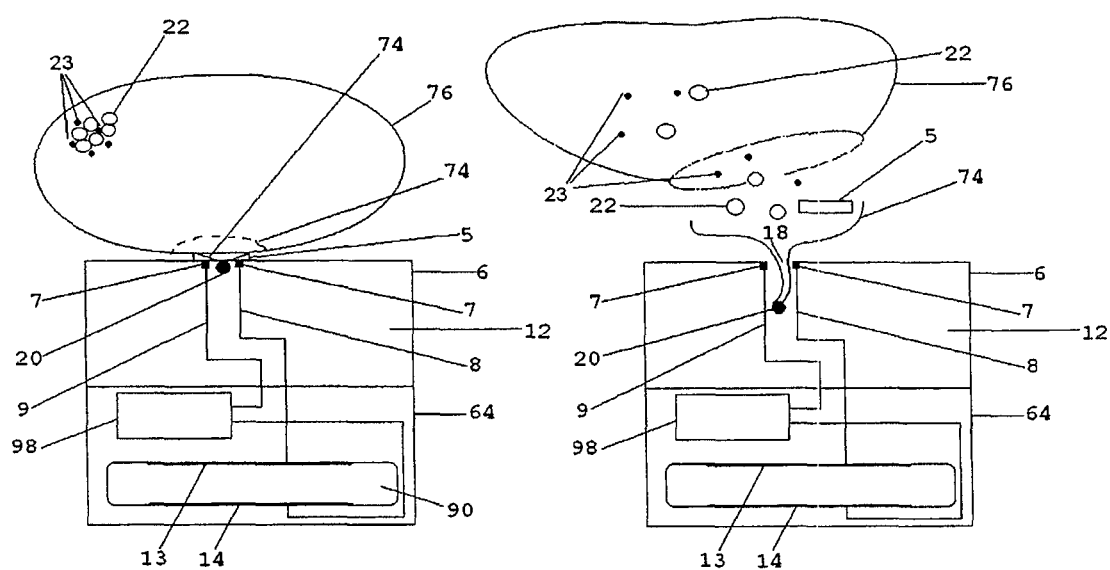
FIG. 5 is a schematic view of a carrier comprising another microelectronic system used to provide feedback for decoupling a container from the carrier.

FIG. 5 schematically illustrates another possible mechanism for providing microelectronic feedback information from the device to the external world about the exact moment of disintegration of the device. Expandable particles 22 (for example, Aquagel by Akina Inc., West Lafayette, Ind.) and dissolvable substance carrying particles 23 (for example, polycaprolactone minispheres impregnated with fluconazole) are stored in absorbable expandable sac 76 (for example, made of Curacel, CuraMedical, Zwanenburg, The Netherlands, or Safil Mesh Bag, B. Braun, Melsungen, Germany), which is kept closed and attached to a carrier 12 by absorbable surgical suture 74 (for example, 5.0 PDS II or 5.0 Vicryl by Ethicon, Cornelia, Ga.). The suture 74 is knotted inside the carrier 12 with a knot 20. The suture 74 enters the carrier 12 through a silicon cap 5, which seals the carrier 12 when the device is held together. Carrier 12 comprises a sealed compartment 64, which hosts a radio-frequency transmitter 98 and a battery 90. The positive terminal 13 of the battery 90 is connected to a wire 8 terminating at the vicinity of the opening 18 sealed by the silicon cap 5 with an electrical terminal 7. Another such terminal is located close to the first, again in the vicinity of the opening 18, and an electrical wire 9 connects it to the positive terminal of the radio-frequency transmitter 98. The negative terminal 14 of the battery 90 is connected directly to the negative terminal of the radio-frequency transmitter 98.

When the surgical suture 74 holding the entire device together disintegrates, the silicon cap keeping the carrier 12 sealed detaches and bodily fluids can now enter the interior of carrier 12, thus short-circuiting the wires 8 and 9. The electric circuit supplying the radio-frequency transmitter 98 is now closed, and the radio-frequency transmitter emits a signal to the external world, informing that the disintegration of the device has taken place. The wires 8 and 9 are kept very close together, so even a small amount of fluid entering the carrier 12 after the sealing cap 5 detaches is sufficient to create a short circuit, thus connecting the radio-frequency transmitter 98 to the battery 90 and to broadcast a signal denoting the exact moment of disintegration. The miniature sealing cap 5 can be made of biocompatible silicon.

Carrier 12 can be made of a wide variety of different materials, which can include, but are not limited to electrically non-conductive silicon and other biocompatible materials such as composite acrylics. The carrier can adopt a wide variety of different shapes. For example, which is not meant to be limiting, carrier 12 can adopt a sphere shape, a cylinder shape, a pyramid shape, a cube shape or combinations thereof. Preferably, the carrier includes one or more sealed compartments 64, as shown in FIG. 4, and FIG. 5, which house the necessary electronics. The electronics can be insulated and may be further encapsulated within the internal cavity of the carrier using electrically non-conductive silicon and other biocompatible materials such as composite acrylics. In one very simple embodiment, the carrier can be a biodegradable sac holding the molecule clusters together, to release them when it biodegrades and is absorbed in the given orifice or cavity in the body.

Figure 6A:
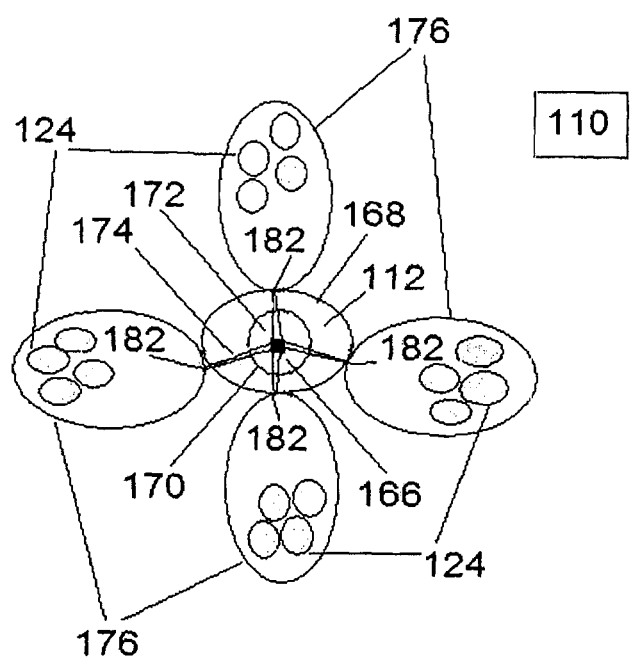
FIG. 6A is a schematic view of another embodiment of a substance delivery device according to the invention in its expanded state, where the expandable particles are impregnated with at least one substance and are contained in permeable expandable containers.
Figure 6B:
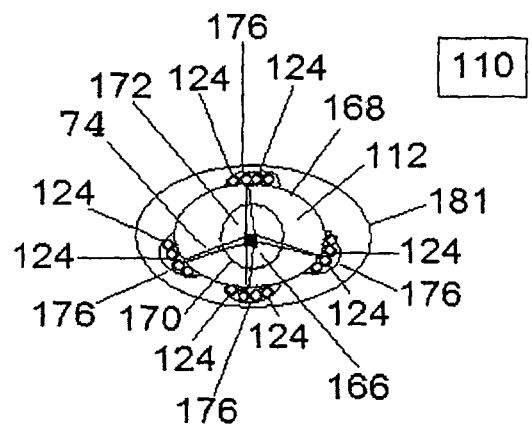
FIG. 6B is a schematic view of the substance delivery device of FIG. 6A in the non-expanded state and encapsulated in a capsule.
Figure 7:
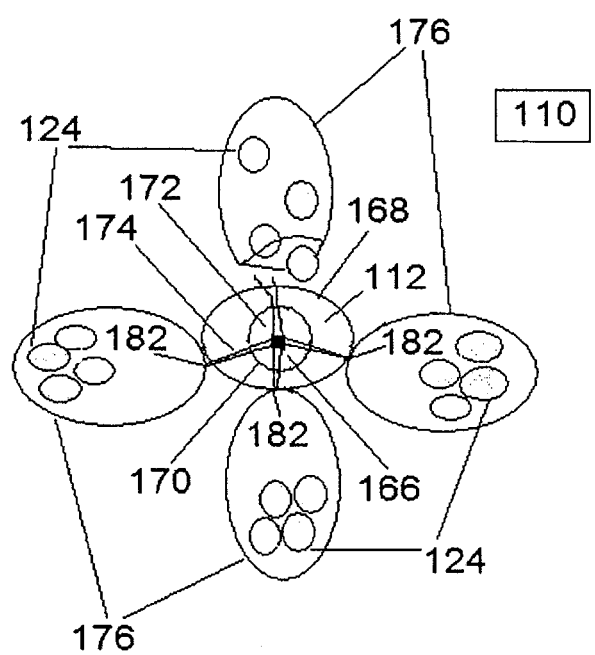
FIG. 7 is a schematic view of the substance delivery device of FIG. 6A where the coupling member comprises absorbable surgical suture that is interrupted at a single point due to its decaying tensile strength.
Figure 8:
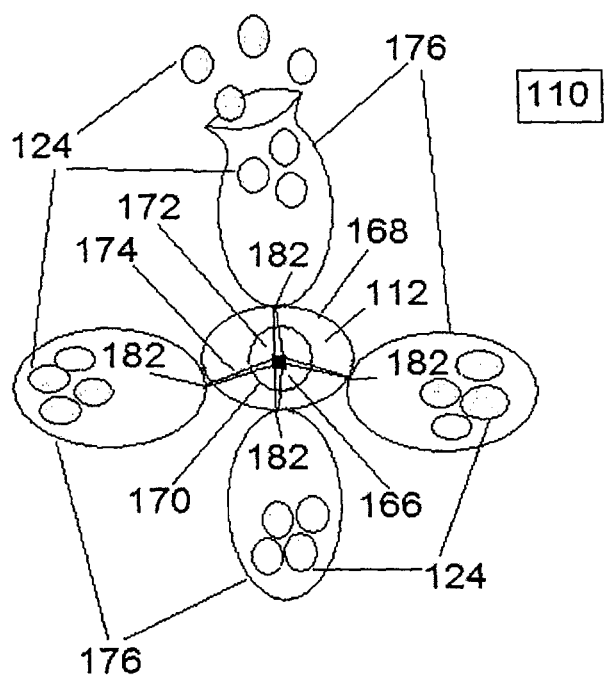
FIG. 8 is a schematic view of the substance delivery device of FIG. 6A where the permeable expandable container is made of an absorbable medical gauze, which eventually disintegrates and releases the particles therein.

Another embodiment of a substance delivery device of the present invention is shown in FIGS. 6-8 and is generally referred to therein as 110. This embodiment is similar to the one illustrated on FIGS. 1-3, except now the expandable particles 124 are impregnated with the specific substance to be delivered. Expandable particles 124 are contained in permeable expandable sacs (containers) 176 and attached to carrier 112 in its interior cavity 172 by coupling members 174. One end of each coupling member 174 is attached to a sac 176 and the other ends are knotted together within the mechanical enclosure 166. In this embodiment, release of the substance commences once the bodily fluid seeps through the permeable sacs 176. FIG. 6B shows the unexpanded device of FIG. 6A encapsulated in capsule 181.

When the device 110 is positioned in the body, bodily fluids allow the expandable particles 122 to swell or expand and the sacs 176 to expand from a first dimension (as shown in FIG. 1B) to a second dimension (as shown in FIG. 1A). In its expanded state, the device 110 will remain in situ in the body until it is disassembled, as discussed below. This allows the substance to be released over a period of time until disassembly of the device.

FIGS. 7 and 8 illustrate two ways that substance impregnated expandable particles 124 may be released from sacs 176.

Figure 9A:
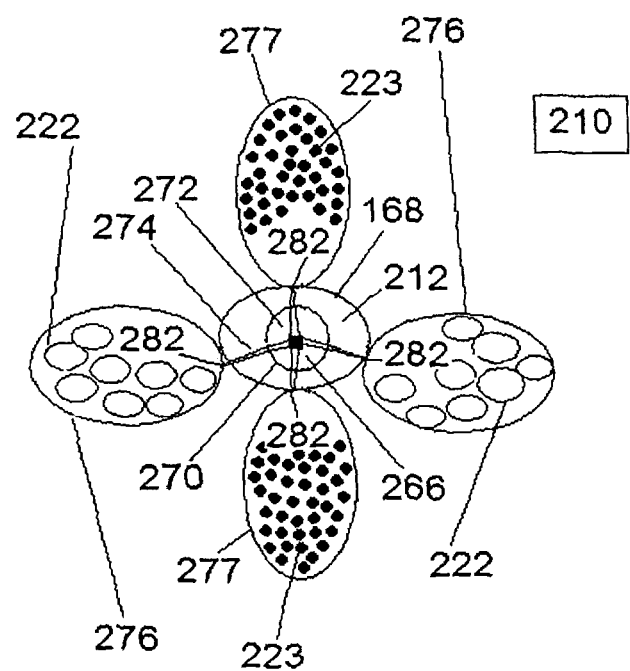
FIG. 9A is a schematic view of one embodiment of a substance delivery device according to the invention in the expanded state, where the expandable particles and the substance carrying particle are contained in separate containers.
Figure 9B:
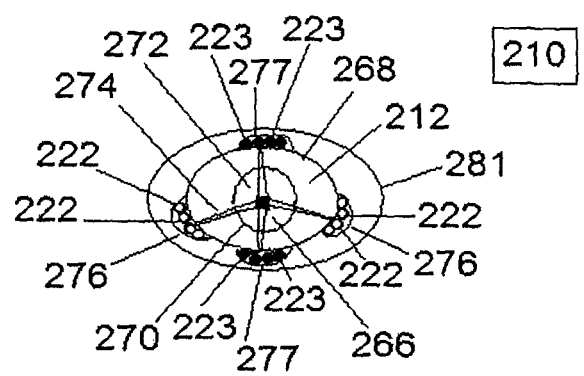
FIG. 9B is a schematic view of the substance delivery device of FIG. 9A in the non-expanded state and encapsulated in a capsule.
Figure 10:
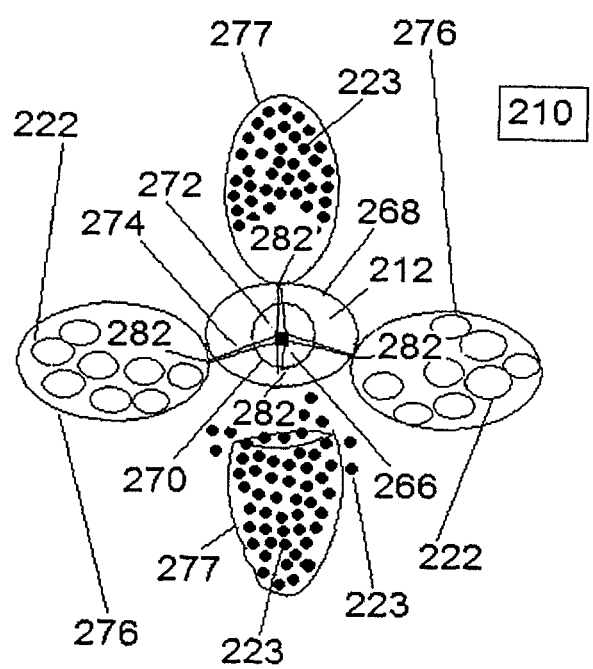
FIG. 10 is a schematic view of the substance delivery device of FIG. 9A where the coupling member that couples one of the substance holding containers to the carrier comprises absorbable surgical suture that is interrupted at a single point due to its decaying tensile strength to release the substance carrying particles.
Figure 11:
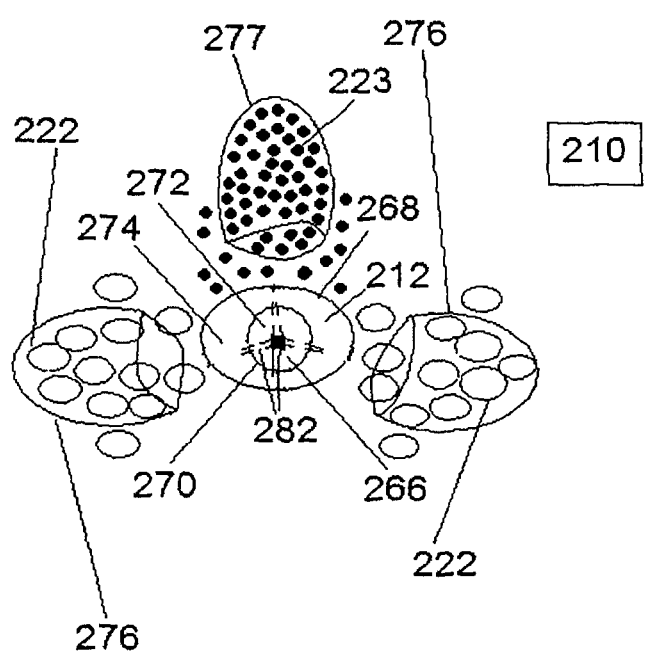
FIG. 11 is a schematic view of the substance delivery device of FIG. 10, in which all containers are coupled to the carrier by a coupling member comprising absorbable surgical suture that is interrupted at a single point due to its decaying tensile strength, thereby decoupling the entire device.

FIGS. 9-11 illustrates another embodiment of the substance delivery device, referred to generally as element 210. Device 210 includes a carrier 212 having an outer surface 268 and an inner surface 270, with the inner surface forming an internal cavity 272. In this embodiment, expandable particles 222 are carried in a plurality of permeable, biocompatible, biodegradable expandable sacs (containers) 276, and dissolvable, substance carrying particles 223 are carried in a plurality of non-permeable, biocompatible, biodegradable substance-holding sacs (containers) 277 that are releasably coupled to the carrier 212 by at least one surgical suture 274 having two ends. Once the device 210 is positioned in the body, bodily fluids allow the expandable particles 222 to swell or expand and the expandable sacs 276 to expand from a first dimension (as shown in FIG. 9B) to a second dimension (as shown in FIG. 9A). In its expanded state, the device 210 will remain in situ in the body until the expandable sacs 276 are decoupled (i.e., the device is disassembled), as discussed below. This allows the substance carrying particles to be released over a period of time until the complete disassembly of the device. The substance carrying particles are generally quite small (e.g., less than a millimeter) so that a large number of them can fit inside substance-holding sacs (containers) 277.

It is understood, however, that a carrier is not always necessary and one or more expandable sacs (containers) carrying the expandable particles and one or more substance-holding sacs (containers) carrying the substance carrying particles can be coupled together by coupling members such as biodegradable sutures.

The decoupling of the sacs 277 from the carrier 212 relies on the separation of the absorbable surgical sutures 274 therefrom as shown in FIGS. 10 and 11. Desirably, sutures 274 are arranged so as to maximize coverage of carrier 212 with sacs 276 and 277. Surgical sutures 274 can be made of a variety of substances and if desired those used to couple the expendables sacs 276 could be made of a slower disintegrating material such as polyglycolic acid and the substance-holding sac sutures could be made from a faster disintegrating material such as cat gut.

In the embodiment illustrated in FIGS. 9-11, sutures 274 can be threaded through internal cavity 272 of the carrier to form a closed loop so that at least one segment of sutures 274 is located within the internal cavity. Double-threaded sutures 274 can enter carrier 212 at a single location 282 for each of sacs 276 and 277 and can be knotted within the mechanical enclosure 266. Of course, if desired, the sutures can be a single thread and more than one entry location per sac can also be used. The sutures connecting each individual sac may or may not be of same long-term tensile decay characteristics, so that full or partial disintegration of the device is achieved. For example, short-term catgut sutures and longer-term polyglycolic acid sutures can be used for various individual sacs to ensure their opening in various times. In addition to the mechanical enclosure 266 holding the suture knots, the internal cavity 272 may or may not host a microelectronic feedback-providing mechanism registering the exact moment of disintegration, as will be discussed below.

In the embodiments illustrated in FIGS. 9-11, expandable particles 222 can comprise any material that can expand when in contact with bodily fluids, and can include, but are not limited to, natural clays (for example, which is not meant to be limiting, Bentonite), microcrystalline hydrogels, polyolefins, polyvinyl alcohol, poly(ethyloxazoline), polyvinylacetate-polyvinylalcohol copolymers, poly(2-hydroxyethylacrylate), poly(2-hydroxyethylmethacrylate), polyacrylic acid, and copolymers thereof, polysaccharides, water soluble proteins, polynucleic acids, or a combination thereof. Expandable particles 222 can be made, if desired, of polyacrylic acid and a crosslinker by solution or suspension polymerization, using the type and quantity of crosslinker to control the swelling capacity and the gel modulus.

Dissolvable, substance carrying particles 223 can comprise any material that has known long-term dissolving properties, such as polycaprolactone, which can be impregnated with, but not limited to, antacid medication omeprazole, antifungal drug fluconazole, etc.

The permeable expandable sacs 276 can be made of an absorbable expandable permeable liner (absorbable medical gauze). The permeable liner should be able to allow bodily fluids to enter sacs 276 and contact the expandable particles 222 to allow for their swelling/expansion. In one embodiment, the permeable expandable sacs 276 can be made from natural cellulose fiber or specialty fiber through spun laced process, spun-bonded polypropylene or absorbable haemostatic oxidized regenerated cellulose (commercially available under the name Curacel), and are initially folded (first dimension), containing the non-expanded expandable particles. It may be desirable that the material itself used to construct sacs 276 be expandable, so as to concurrently expand with the expandable particles 222. As a safety feature, sacs 276 may be made of biodegradable material, so as to allow for biodegradation after several days or weeks. Similarly, dissolvable, non-permeable sacs 277 can be made from the same material, but with much smaller mesh (pore) size, making them non-permeable to bodily fluids. Moreover, suture 274 can also be made of an absorbable biocompatible material, which can include, but is not limited to, polycaprolactone, polyglycolide, polylactide, or combinations thereof (commercially available under the names Selecture PLL and Selecture VEH by Schering-Plough Animal Health Corporation), or the like, each of which is absorbable and has specific tensile strength decaying characteristics that are not necessarily the same. Thus, if sutures of different tensile strength decaying characteristics are used, gradual partial disintegration of the device can result. It is imperative for sutures 274 to be capable of withstanding the maximum physiological forces existing in the given orifice or cavity in the body to prevent release of sacs 276 before the said suture biodegrades sufficiently so that the decoupling takes place.

The non-permeable sacs 277 containing the substance carrying particles 223 should be biocompatible and can be made long-term biodegradable for additional safety. Only when their attachment to the carrier is severed in a controlled fashion, the sacs open and the dissolving of the substance-impregnated particles 223 starts. A plurality of such non-permeable sacs 277 containing particles 223 ensures that substance delivery control can be intermittent (if the next sac is opened some time after the substance-impregnated particles contained in the first opened sac are dissolved) or continuous (if the next sac is opened immediately after the substance-impregnated particles contained in the first opened sac are dissolved). The non-permeable sacs 277 can be made from the same material as the permeable sacs 276, but with much smaller pore (or mesh) size so that body fluid molecules cannot enter in it while it is held tightly closed by suture 274.

The substance releasing device can also comprise a decoupler to decouple the sacs 276 or 277 or both from the carrier 212. Examples of decouplers that can be used include, but are not limited to, a cutting member or melting member or both, which will cut and/or melt the coupling sutures, the sacs holding the particles, or both. Once suture/s 274 is/are disrupted, sacs 276 and 277 can become separated from the carrier 212 and open, thereby releasing their contents (i.e., the expandable particles and the substance carrying particles). Since each of these particles are appropriately sized, they can individually exit the orifice or the cavity in the body in a natural way, or be absorbed by the body. The sutures 274 can be disrupted either sequentially or simultaneously.

FIG. 9B illustrates the substance releasing device 210 in its unexpanded configuration contained in a shell 281. Both expandable particles 222 and substance carrying particles 223 are dry so that both the permeable expandable sacs 276 and the substance-holding sacs 277 can be held in a folded conformation and contained in shell 281 to facilitate placement in the given body cavity or orifice. Shell 281 can be made of a variety of different materials, which can include, but are not limited to, pH-sensitive materials that will only dissolve under certain conditions, for example, the pH of the given body cavity. The material used to make the shell can be the same material, for example, gelatine or cellulose, used to make pharmaceutical capsules known in the art. Various sizes of shells can be used depending on the volume of the specific body cavity and the route to reach it.

FIG. 10 illustrates the decoupling and opening of one of the two non-permeable sacs 277 by disrupting the suture 274 thereby allowing the sac held to the carrier at location 282 to open and release the substance carrying particles.

FIG. 11 illustrates the subsequent release of substance carrying particles from non-permeable substance-holding sac 277, which occurs after the first release of substance carrying particles from the first substance-holding sac. Thus, substance delivery has been controlled by delivering the substance at two different time intervals. The second delivery commences with the opening of the second non-permeable substance-holding sac 277 by disrupting another suture 274 holding the said second sac, and the release of a second set of substance carrying particles in situ. After all of the substance carrying particles have been released, the device further disintegrates by decoupling all remaining sutures 274 that couple the permeable expandable sacs 276 to the carrier 212, thus decomposing the entire device to components that can be absorbed by the body or freely exit the orifice or the cavity in the body in which the device was positioned.

Figure 12:
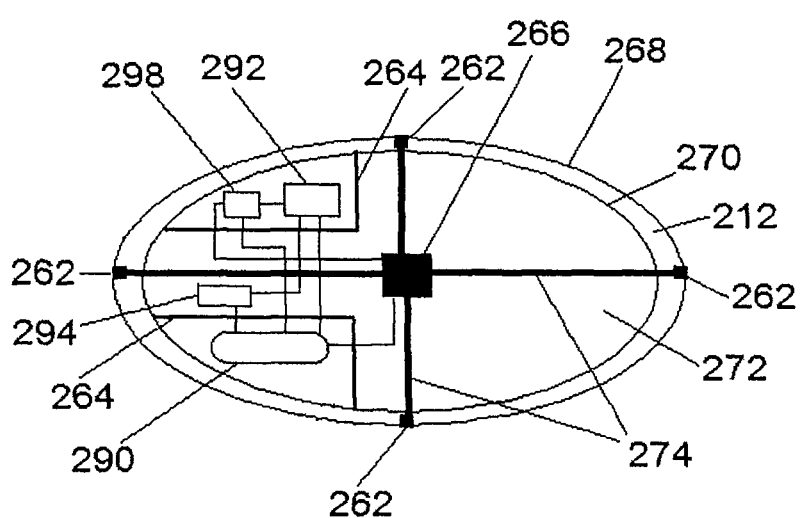
FIG. 12 is a schematic view of a microelectronic system used in a substance delivery device of the present invention to provide feedback about certain physiological conditions in the carrier, thereby controlling the release of a substance in the given orifice or body cavity where the device has been positioned.

FIG. 12 illustrates a feedback mechanism which first measures a certain physiological quantity, for example pH, with a specific physiological sensor, microsensor 294, located in the carrier 212, and then determines whether to release a given substance-holding sac 277 containing substance carrying particles 223 (as shown in FIG. 11) based on whether the measured physiological quantity warrants the release. The feedback mechanism implements the decision to release another substance-holding sac in a controlled fashion under the direction of the microcontroller unit 298. An amplification and conditioning circuit 292 connects the microsensor 294 to the microcontroller. The microcontroller unit 298 controls a matrix of decouplers, microheaters 266, which can melt the sutures 274 either simultaneously or sequentially. This electronic control is supplied with a battery 290 and the sutures 274 are threaded to be attached to the sacs through the holders 262, which can be implemented by rigid biocompatible silicon sealant. The electronic components and the battery are positioned in hermetic compartments 264.

The microsensor 294 can be implemented using a variety of sensing technologies, including, but not limited to, electrochemical, chemical, physical, electrophysical, electronic, impedance, etc. for detecting various physiological parameters. For example, for pH monitoring, an antimony microsensor can be utilized as described in Geus et al., *Eur J Gastroenterol Hepatol.* 1995 Jan; 7(1):29-35.

The microcontroller 298 can be adopted from many existing brands developed by various manufacturers, which include, but are not limited to, Analog Devices (Norwood, Mass.), Maxim Integrated Products (Sunnyvale, Calif.), Microchip Technology (Chandler, Ariz.), etc., or can be custom-designed using the technology described in Mayr et al., Basic design and construction of the Vienna FES implants: existing solutions and prospects for new generations of implants. *Medical Engineering & Physics* (2001) 23: 53-60, incorporated herein by reference.

The amplification and conditioning unit can be implemented using an appropriate low-noise analog microelectronic circuitry, which produces outputs that can be directly fed to the microcontroller.

Carrier 212 can be made of a wide variety of different materials, which can include, but are not limited to electrically non-conductive silicon and other biocompatible materials such as composite acrylics. The carrier can adopt a wide variety of different shapes. For example, which is not meant to be limiting, carrier 212 can adopt a sphere shape, a cylinder shape, a pyramid shape, a cube shape or combinations thereof. Preferably, the carrier includes one or more sealed compartments 264, as shown in FIG. 12, which house the necessary measurement and control electronics. The electronics can be insulated and may be further encapsulated within the internal cavity of the carrier using electrically non-conductive silicon and other biocompatible materials such as composite acrylics.

It is understood that a coupling member, such, as a suture, can also be coupled to the outer surface of a carrier in a wide variety of different ways, for example, but not limited to, by a mechanical force and wrapping, or combinations thereof. Decouplers, which can be used to decouple the coupling member from the outer surface of the carrier include, but are not limited to, means for producing a gradual pH-based, enzyme-based, or other type of biodegradation of the material providing the mechanical force to hold the device together, of the material utilized to form the sacs containing the clusters of molecules, or a combination thereof. The feedback to the external world providing information on the exact moment of administration of certain substances carried by substance carrying particles comprises microelectronic devices, which can include, but are not limited to, sensors, microcontrollers, RF transmitters, and batteries. For example, which is not meant to be limiting, radio-frequency receivers external to the body can receive a signal from the encapsulated antimony-based sensor indicating that the pH level in the body cavity has dropped below a certain pre-determined level, and thus provide precise timing for opening a non-permeable substance-holding sac carrying antacid containing particles, for example polycaprolactone granules impregnated with the antacid drug omeprazole. This would increase the pH level in the body cavity to an acceptable level, but if after awhile this level drops again, another non-permeable substance-holding sac can be controlled to open. The process can continue intermittently or continuously until all non-permeable sacs are exhausted. Only then the permeable expandable sacs containing the expandable particles are controlled to open, and the entire device is thereby disassembled.

With reference now to FIGS. 13 and 14, this embodiment illustrates a possible implementation of a substance delivery device without a carrier, using one or multiple permeable disintegratable expandable containers (sacs) filled with expandable particles impregnated with specific substance or substances. In the alternative, the substance could be present in substance carrying particles, which particles would also be contained in the expandable sac. Further, in the alternative, formulated granules of the substance could be introduced into the expandable sac, which granules can be fast release, controlled release or delayed release granules. Further, in the alternative, the substance carrying particles could be contained in their own substance-holding container (sac).

FIGS. 13A and 13B illustrates a single permeable expandable container (sac) 312 containing dry expandable particles 314 and therefore in a non-expanded first dimension. The device 310 can then be packed into a gelatin capsule 381 as shown in FIG. 13B. After the capsule is positioned in situ in the appropriate cavity or orifice in the body, the device expands (FIG. 13C) due to the swelling of the expandable particles 314', which are also impregnated with a specific substance or substances. Once the device 310 is in the expanded or second dimension, the device commences the timed delivery of the specific substance or substances. At a predetermined moment, the sac container 312 disintegrates, as it has been made from an absorbable biocompatible medical textile yarn such as, but not limited to, oxidized regenerated cellulose, polyvinyl alcohol, or polyglycolic acid. FIG. 13D illustrates the moment of disintegration, at which time the swelled expandable particles 314' are released in a given body cavity, for example the stomach. When being released in the stomach, the particles are generally designed not to exceed about 1.0 cm in diameter and, optimally not exceeding about 0.5 to about 0.6 cm in diameter. in order to facilitate their passage through the entire gastrointestinal tract without creating any obstruction.

Figure 14A:
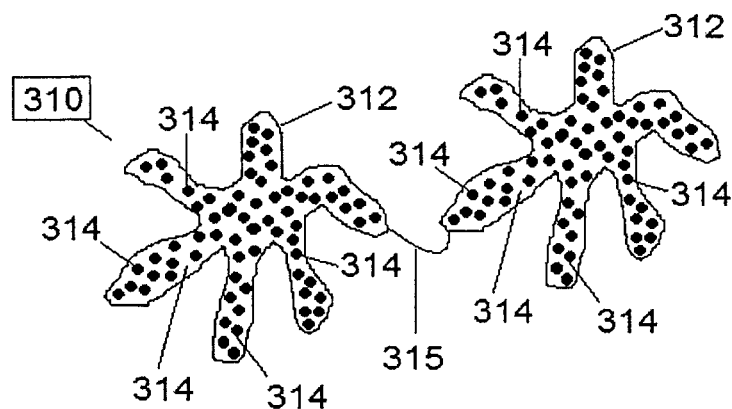
FIG. 14A is a schematic view of an embodiment of an unexpanded substance delivery device comprising two permeable expandable containers, each filled with dry expandable particles impregnated with at least one specific substance and coupled by a coupling member comprising an absorbable surgical suture such as catgut or polyglycolic acid.

FIG. 14A illustrates a substance delivery device 310 in its first dimension (unexpanded) comprising two permeable expandable containers 312 of FIG. 13A coupled together by coupling member (absorbable surgical suture) 315. It is understood, of course, that more than two containers 312 can be coupled together to form a device of the present invention.

Figure 14B:
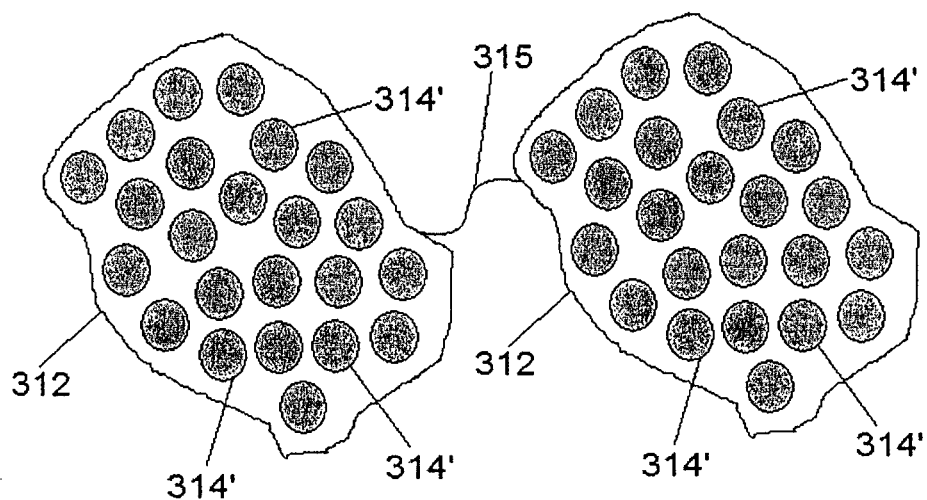
FIG. 14B is a schematic view of the expanded substance delivery device of FIG. 14A.

FIG. 14B depicts the device in a given body cavity, for example in the stomach, in the second or expanded dimension, where the expandable particles that have been impregnated with a specific substance or substances have fully expanded and the medication delivery has started. The two sub-bezoars are held together by an absorbable surgical suture 315, upon the disintegration of which the entire structure falls apart after a predetermined time has elapsed and the expanded particles are released in the given body cavity, for example, in the gastrointestinal tract.

Figure 15:
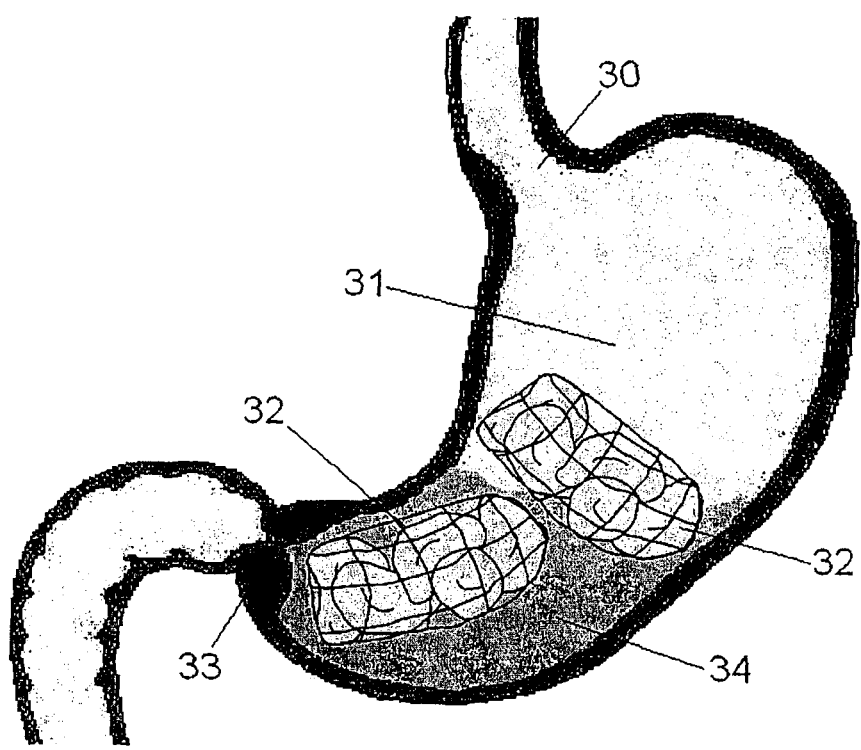
FIG. 15 is a schematic view of the stomach containing two substance delivery devices of the present invention in the expanded configuration.
Figure 16:
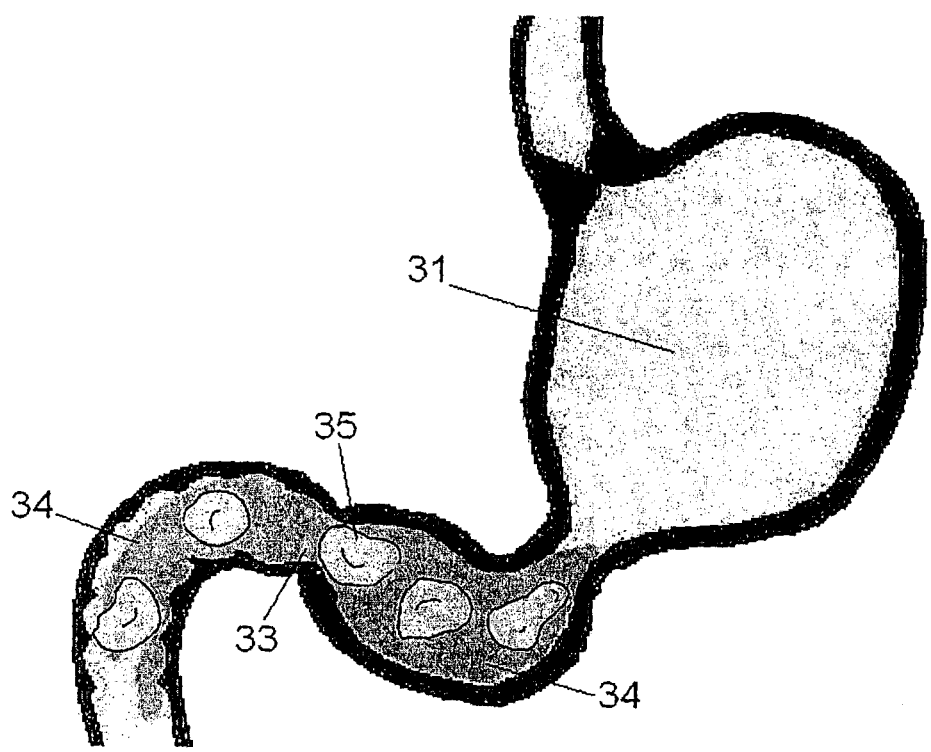
FIG. 16 depicts the dispersion of the swelled expandable particles of the devices in FIG. 15 in the stomach and their exit to the duodenum and through to the end of the gastrointestinal tract (the anus) after the disintegration of the permeable expandable containers.

FIGS. 15-16 illustrate that the substance delivery devices of the present invention can be used not only as a platform for controlled delivery of specific substances, but as a tool for volume reduction of the stomach from within the organ, thus reducing the appetite of a patient. After swallowing a capsule containing a device of the present invention, the latter passes through the gastroesophageal junction 30 and reaches the stomach 31, where the gastric fluid 34 dissolves the capsule and allows the device to expand to a bezoar 32 of a size that precludes its expulsion through the pylorus 33. Several such bezoars can be simultaneously present in the stomach to enhance the volume-reducing effect. FIG. 16 illustrates the disintegration of the device thereby releasing the expanded expandable particles 35. These expanded expandable particles can be impregnated with medication similarly to the concept illustrated in FIGS. 6-8. In this particular embodiment, a single permeable sac fulfills the role of a carrier and is the container for the expandable particles. It is the disintegration of this container after a predetermined period of time that releases the expanded expandable particles 35 into the stomach. The individual expanded expandable particles 35 are of size that can easily pass through the pylorus 33 when it opens during the regular and normal operation of the stomach 31, in which gastric fluid 34 along with other gastric content is expelled to the duodenum and through to the lower gut.

FIG. 17A schematically illustrates another embodiment of a substance delivery device 410 whereby the specific substance is delivered from within carrier 412, which delivery begins after the disintegration of the device. In this embodiment, substance is also contained in absorbable expandable sacs or containers 476, however, it is understood that the substance may be solely contained within carrier 412.

Expandable particles 422 (for example, Aquagel by Akina Inc., West Lafayette, Ind.) and dissolvable substance carrying particles 423 (for example, polycaprolactone minispheres impregnated with fluconazole) are contained in at least one absorbable expandable sac 476 (for example, made of Curacel, CuraMedical, Zwanenburg, The Netherlands, or Safil Mesh Bag, B. Braun, Melsungen, Gernany), which sacs are kept closed and attached to carrier 412 by absorbable surgical suture 474 (for example, 5.0 PDS II or 5.0 Vicryl by Ethicon, Cornelia, Ga.). The suture 474 is knotted inside the carrier 412 with a knot 420. The suture 474 enters the carrier 412 through a silicon cap 450, which seals the carrier 412 when the device is held together.

Carrier 412 comprises a first sealed compartment 484, which contains the specific substance 483 to be delivered, a second sealed compartment 464, which hosts a microelectronic control circuit 498, and a battery 490. The first sealed compartment 484 is sealed with a biocompatible sealant cap 481 held by an absorbable suture 482 attached rigidly to the microelectronic control circuit 498. The positive terminal 413 of the battery 490 is connected to a wire 480 terminating at the vicinity of the opening 418 sealed by the silicon cap 450 with an electrical terminal 470. Another such terminal is located close to the first terminal, again in the vicinity of the opening 418, and an electrical wire 490 connects it to the microelectronic control circuit 498. The negative terminal 414 of the battery 490 is connected directly to the negative terminal of the microelectronic control circuit 498.

FIG. 17B depicts the moment of disintegration of device 410. When the surgical suture 474 holding the entire device together disintegrates, the silicon cap keeping the carrier 412 sealed detaches and bodily fluids can now enter the interior of carrier 412, thus short-circuiting the wires 480 and 490. The electric circuit supplying the pre-programmed microelectronic controlled circuit 498 is now closed, and the latter becomes active. For example, the microelectronic control circuit can contain a timer and a microheater, which in a pre-determined moment interrupts the biocompatible absorbable suture 482, and this in turn releases a sealant cap 481 made for example from biocompatible silicon, thus creating an opening 485 of the compartment 484 within the carrier 412, from which the specific substance 483 is released.

According to another embodiment of this invention, there is provided a dosage form delivering at least one specific substance in the body including at least one substance delivery device of the present invention and, if desired, a pharmaceutically acceptable excipient such as binders, fillers and disintegrants, for example, starch. The pharmaceutical dosage form may take various forms, which include, but are not limited to, liquids, soft substances, powder-like substances, and hard pharmaceutical substances such as soft capsules, hard capsules and tablets. In one embodiment, the pharmaceutical dosage form is a capsule. In another embodiment, the capsule can be coated with a pH-sensitive coating. The pH-sensitive coating may prevent dissolution until the targeted body cavity is reached, to prevent contact between the expandable particles and bodily fluids from other cavities that would generally have different pH environment.

Example 1

Technique for Impregnating a Substance Such as a Therapeutic Agent into an Expandable Particle A therapeutic agent can be impregnated into a given polymer using the methodology described in N. E. Cooke, C. Chen, *Inter. J. Pharm.*, 1995, 115(1): 17-27; and in Li et al., *J. Pharm. Pharmaceut. Sci.*, 9(2):238-244, 2006, both of which are incorporated hereto by reference Briefly, a rod or sheet, made of a glassy polymer matrix containing a given therapeutic agent, is placed in contact with a solvent. As the interface advances, the therapeutic agent suspended in the matrix will be released and diffused away into the solvent. A superabsorbent polymer matrix is then added to the solvent. Originally, the concentration downstream of the interface (in the superabsorbent polymer) is lower than that upstream of the interface (in the glassy polymer), thus, a sharp break exists in both sides. Progressively with time, the interface moves further toward the unpermeated superabsorbent polymer matrix. Hence, the path for therapeutic agent diffusion from the interface to the sink gets correspondingly longer. This results in a gradual accumulation of the therapeutic agent in the superabsorbent polymer and an increased concentration downstream of the interface. Eventually, when the path for drug diffusion reaches a 'critical length', the concentration downstream of the interface will become equal to that upstream of the interface. Beyond the critical point, the moving front will not affect the concentration profile due to the relative slower rate for the therapeutic agent diffusion. Thus, the superabsorbent polymer matrix would be impregnated with the desired therapeutic agent in a quantifiable concentration. Subsequently, the superabsorbent polymer matrix is left to dry and is split into clusters of desired size (usually with a diameter in the range of hundreds of micrometers).

It is understood that the above methodology can also be used to impregnate a specific substance in other, non-expandable particles as well. Further, similar techniques can be used to impregnate a specific substance different from a therapeutic agent in expandable particles.

While the invention has been described in conjunction with the disclosed embodiments, it will be understood that the invention is not intended to be limited to these embodiments. On the contrary, the current protection is intended to cover alternatives, modifications and equivalents, which may be included within the spirit and scope of the invention. Various modifications will remain readily apparent to those skilled in the art.

What is claimed is:

1. A device for delivering a pharmaceutical substance in situ in a body, the device comprising
  (a) a carrier (212),
  (b) coupling members (274) for releaseably coupling containers to the carrier (212),
  (c) at least one permeable expandable container (276) having a first dimension and a second dimension and containing at least one expandable particle (222) comprising a swellable material capable of expanding when contacted with a bodily fluid to expand the container from the first dimension to the second dimension so that the device remains in situ for a period of time sufficient to achieve the desired delivery of the pharmaceutical substance; and
  (d) at least one substance-holding container (277) consisting essentially of a biocompatible sac and the pharmaceutical substance to be delivered.

2. The device as claimed in claim 1, wherein the coupling member (274) is selected from the group comprising an absorbable biodegradable surgical suture, a piece of biodegradable medical gauze, an absorbable net-like nanostructure, biocompatible glue or combinations thereof.

3. The device as claimed in claim 1, wherein the carrier (212) further comprises a controller (298) for controlling the release of the pharmaceutical substance from the at least one substance-holding container (277).

4. The device as claimed in claim 1, wherein the pharmaceutical substance is in the form of a substance-carrying particle (223).

* * * * *